United States Patent
Sinn

(10) Patent No.: US 7,781,406 B2
(45) Date of Patent: Aug. 24, 2010

(54) PRODUCTION AND USE OF THE METHOTREXATE-ALBUMIN CONJUGATE AS AN IMMUNOSUPPRESSIVE AGENT IN GVHD

(75) Inventor: Hannsjörg Sinn, Wiesloch (DE)

(73) Assignee: Albupharm Heidelberg GmbH & Co. KG, Heidelberg (DE)

( * ) Notice: Subject to any disclaimer, the term of this patent is extended or adjusted under 35 U.S.C. 154(b) by 0 days.

(21) Appl. No.: 10/594,876

(22) PCT Filed: Apr. 1, 2005

(86) PCT No.: PCT/EP2005/003460

§ 371 (c)(1),
(2), (4) Date: Sep. 29, 2006

(87) PCT Pub. No.: WO2005/094895

PCT Pub. Date: Oct. 13, 2005

(65) Prior Publication Data

US 2007/0231338 A1     Oct. 4, 2007

(30) Foreign Application Priority Data

Apr. 2, 2004    (DE) ................ 10 2004 016 355

(51) Int. Cl.
*A61K 31/4985*    (2006.01)
*A61K 38/38*    (2006.01)
(52) U.S. Cl. .................................. 514/21; 514/249
(58) Field of Classification Search ............ None
See application file for complete search history.

(56) References Cited

U.S. PATENT DOCUMENTS

| | | | |
|---|---|---|---|
| 5,688,488 A * | 11/1997 | Low et al. ............... | 424/1.69 |
| 5,993,805 A * | 11/1999 | Sutton et al. ............ | 424/94.1 |
| 6,210,677 B1 * | 4/2001 | Bohannon ............... | 424/193.1 |
| 6,491,923 B1 * | 12/2002 | Dave et al. ............. | 424/193.1 |
| 2003/0032631 A1 * | 2/2003 | McDonald et al. ....... | 514/178 |
| 2003/0149045 A1 * | 8/2003 | Fatih ..................... | 514/251 |
| 2003/0225010 A1 * | 12/2003 | Rameshwar ............. | 514/44 |

FOREIGN PATENT DOCUMENTS

| | | | |
|---|---|---|---|
| CA | 2289448 | | 5/1998 |
| DE | 41 22 210 A1 | | 1/1993 |
| EP | 0 282 057 A | * | 9/1988 |
| WO | 0 879 604 A1 | | 9/1997 |

OTHER PUBLICATIONS

Vallera et al. Anti-graft-versus-host disease effect . . . Blood. 1996, vol. 88, No. 6, pp. 2342-2353.*
Wolff et al. Methotrexate-albumin and aminopterin-albumin . . . Blood. 2003, vol. 102, No. 11, p. 404b.*
Wolff et al. Methotrexate-albumin and aminopterin-albumin . . . Blood. Vol. 102, No. 11, p. 404b, (2003).*
Bures et al. The use of protein as a carrier of methotrexate . . . Neoplasma. 1988, vol. 35, No. 3, pp. 329-342.*
Kratz. Drug conjugates with albumin and transferrin. Expert Opinion On Therapeutic Patents. 2002, vol. 12, No. 3, pp. 433-439.*
Shen et al. Selective killing of Fc-receptor-bearing complex . . . Proceedings of the National Academy of Science USA. Mar. 1984, vol. 81, pp. 1445-1447.*
Vallera et al. Anti-graft-versus-host disease effect . . . Blood. Vol. 88, No. 6, pp. 2342-2353, (1996).*
Levy, Louis, "Effect Cyclophosphamide and Methotrexate on the Field Effect or Unresponsiveness Obersved in the Rat and Mouse GvHR," *Chem Abstracts*, vol. 83:157912 (1975).
Stehle G.et al., The loading rate determines tumor targeting properties of methotrexate-albumin conjugates in rats, Anti-Cancer Drugs, 1997, pp. 677-685, vol. 8.

* cited by examiner

*Primary Examiner*—Jeffrey E Russel
(74) *Attorney, Agent, or Firm*—Ping Wang; Morris, Manning & Martin LLP

(57) ABSTRACT

A method for modulating a transplantation-associated immune response in a subject is disclosed. The method comprises administering to the subject an effective amount of a conjugate comprising a carboxyl group-containing organic compound and albumin, wherein the carboxyl group-containing organic compound is a cytostatic or an immunosuppressant. A method for preparing the conjugate is also disclosed. The method includes activating the carboxyl group-containing organic compound with 1-ethyl-3-(3-dimethylaminopropyl) carbonyldiimide in an organic solvent, and reacting activated carboxyl group-containing organic compound with albumin, wherein the carboxyl group-containing organic compound is a cytostatic or an immunosuppressant.

7 Claims, 2 Drawing Sheets

PRODUCTION AND USE OF THE METHOTREXATE-ALBUMIN CONJUGATE AS AN IMMUNOSUPPRESSIVE AGENT IN GVHD

The present invention relates to the use of active substance-protein conjugates for modulating and, in particular, for preventing transplantation-associated immune responses. In addition, novel, advantageous processes for preparing the conjugates which can be employed according to the invention are provided.

Active substance-protein conjugates are used in order to obtain longer half-lives on administration of therapeutic or/and diagnostic active substances (cf. DE 41 22 210 A1 or WO 96/32133) by coupling exogenous active substances to an endogenous protein. In the treatment of neoplastic diseases, the uptake of proteins by proliferating tumor cells is utilized for concentrating the active substance bound to proteins in such cells, whereas healthy tissue has no inducement to protein uptake. Concentrating the active substances in tumor cells can thus be achieved.

Thus, DE 41 22 210 A1 describes conjugates of a tumor-active compound which has at least one carboxyl group, and of a protein which is not regarded by the organism as exogenous, with the protein being in native form. These conjugates are used for the treatment of neoplastic diseases but not employed for transplantation-associated immune responses. A process for preparing such conjugates is also described.

European patent application EP 0 879 604 A1 discloses conjugates comprising a folic acid antagonist and a carrier, preferably native protein, processes for their preparation, and their use for the treatment of neoplastic diseases, inflammations and/or autoimmune diseases, but not for the treatment of transplantation-associated immune responses.

Allogeneic bone marrow transplantations (BMT) are increasingly being employed in high-dose radiotherapy, the therapy of hematological/oncological diseases, for example of leukemias, lymphomas, aplastic anemia or renal cell carcinomas. However, they are still associated with a considerable direct and indirect morbidity and mortality, caused in particular by immunological complications, for example in the form of graft-versus-host disease (GVHD), thus limiting their wider applicability.

Levy discloses in his publication (Chem. Abstracts 83 in Agents and Actions, 1975, 5th edition, No. 3, pp. 268-271) the immunosuppressive action of cyclo-phosphamide and methotrexate, which are immuno-modulating medicaments, on graft-versus-host disease (GVHD) in the rat and mouse models.

Although the immunomodulating medicaments employed to date have in some cases been able to reduce the mortality of acute and chronic GVHD, they fail in some patients and in some cases are also associated with considerable side effects. The risk of systemic infection as a consequence of broad immunosuppression predominates here. There are in addition a number of medicament-specific organ toxicities of the medicaments employed to date, which lead to complications in particular with the frequently lengthy use over weeks or months.

One object of the present invention was therefore to provide a pharmaceutical with which the difficulties occurring in the prior art can be overcome and with which in particular the survival rate in allogeneic bone marrow transplantations can be improved.

This object is achieved according to the invention through the use of a conjugate comprising a carboxyl group-containing organic compound and a protein for producing a pharmaceutical for modulating a transplantation-associated immune response.

It has now been found that conjugates of carboxyl group-containing organic compounds and proteins, in particular albumin or transferrin, can also be employed successfully for modulating transplantation-associated immune responses.

The conjugates employed according to the invention comprise a carboxyl group-containing organic compound which is in particular an active substance, more preferably a low molecular weight active substance having a molecular weight of $\leq 1000$ Da and more preferably of $\leq 500$ Da. The active substance is particularly preferably a cytostatic or an immuno-suppressant. Methotrexate or aminopterin is particularly preferably employed, and methotrexate is most preferably employed. The folic acid antagonist methotrexate or 4-amino-4-deoxy-10-methylfolic acid ($C_{20}H_{22}N_8O_5$) is a cytostatic. This active substance is a proven low molecular weight active substance for prophylaxis of GVHD and has a dose-dependent immunosuppressive action. In the conjugate form which is administered according to the invention it is possible to achieve a high concentration and, in particular, an immunosuppressive amount of the active substance at the desired site of action while providing overall less administration and thus less side effects.

The conjugate of the invention comprises proteins in native form. The protein preferably has as molecular weight of $\geq 18\,000$ Da, more preferably $\geq 50\,000$ Da. It is beneficial to select, depending on the patient to whom the conjugate is to be administered, an appropriate native protein, in particular albumin, that is to say for example for administration to humans a human protein and for administration to animals, for example mice, a corresponding mouse protein. Suitable proteins are for example albumin, in particular human serum albumin (HSA) or transferrin. Albumin is particularly preferably employed as protein.

The covalent bonding of low molecular weight active substances to the macromolecule albumin is described for example in DE 41 22 210 A1 or in WO 96/32133, the conjugate therein being employed for the treatment of neoplastic diseases and/or for the treatment of inflammatory, infectious and/or skin diseases. It has now been found that such conjugates are also excellently suitable for the prophylaxis or treatment of transplantation-associated immune responses such as, for example, GVHD. The conjugates employed according to the invention enable a distinctly more targeted and optimized effect, in particular of cytostatics and other active substances, in inflammatory tissue and proliferating metabolically active cells. The relevant cells in a transplantation are reactive lymphocytes and cells of the mononcyte phagocytic system (MPS), in this case in particular the dendritic cells of the reactive lymphatic tissues. It has additionally been found, surprisingly, that the conjugates employed according to the invention do not cause a general immunosuppression in the whole organism but, on the contrary, bring about a selective modulation and, in particular, suppression of transplantation-associated immune responses and preferably of GVHD.

The optimized uptake is brought about in particular by favorable kinetics of albumin, for example with a plasma half-life of about 19 days in humans, and by the importance of albumin as a potential nutrient for proliferating cells. Whereas on administration of free active substances the proportion of the active substances which acted only briefly in the cells relevant for transplantation-associated immune responses is very low, the conjugates of the invention make it possible for the active substance to be concentrated in the relevant cells over a long period.

Owing to the long biological half-life for example the activity proportion in the blood of the MTX-HSA conjugate is about 300 times larger than that of the low molecular weight MTX alone.

Unknown substances are normally rapidly excreted or intercepted in the body, for example water-soluble compounds are excreted via the kidneys, or water-insoluble compounds are intercepted by the liver within a few minutes. Endogenous proteins, for example albumin, by contrast have a long residence time in the organism. It is present in large quantities in tissues and not immunogenic. Coupling of active substances which are intrinsically removed rapidly from the body to such endogenous proteins masks the active substances from the excretion and interception mechanisms of the body, and they can thus likewise achieve a long half-life in the body. However, it is possible thereby to administer only small quantities of active substance, and thus virtually completely to eliminate any side effects occurring. There are virtually no toxic effects on healthy tissue or organs, because normal cells have no inducement to protein uptake. It has now been found, surprisingly, that the conjugates of the invention are taken up not only in tumor cells but also in cells relevant for transplantation-associated immune responses, and thus lead to an active substance being concentrated in these cells.

Owing to the long residence time of the conjugates employed according to the invention in the body it is possible to carry out a prophylaxis or/and treatment of GVHD successfully even if the intervals between the individual administrations of the conjugate are more than 5 days, preferably more than 10 days, in particular more than 13 days or even more than 20 days. It is possible in this way to administer an appropriate maintenance dose to patients, e.g. every 2 to 3 weeks, for years, without the occurrence of side effects.

The conjugates of the invention comprising an active substance, preferably methotrexate, covalently bonded to a protein, in particular to albumin, are suitable for the modulation and in particular for the prevention of transplantation-associated immune responses. Modulation means in this connection herein any influencing or alteration of the immune responses, and in particular an enhancement or reduction of the immune response, in particular by at least 10%, preferably by at least 20%. A substantial reduction particularly preferably by for example at least 50%, more preferably by at least 70% or a prevention of the transplantation-associated immune responses is achieved. This effect opens up a wide range of uses for the conjugates of the invention for preventing immunological complications associated with transplantations, in particular with allogeneic or autologous bone marrow transplantations, but also for preventing recipient-mediated rejection reactions associated with organ transplantations, in particular with unrelated donor organ transplantations of, for example, kidney, heart or liver.

The conjugates of the invention can therefore advantageously by employed for the treatment or/and prophylaxis of GVHD and in particular of acute or chronic GVHD.

The conjugates of the invention are particularly suitable for administration to humans.

The conjugates of the invention are ordinarily administered intravenously. The dose unit administered for an effective treatment is preferably 0.1 to 1000 mg of conjugate per kg of body weight, in particular 1 to 100 mg of conjugate per kg of body weight. It is possible to achieve an effect even with a lower dosage of the conjugates of the invention, e.g. of ≦5 mg and in particular of ≦3 mg of conjugate per kg of body weight. The molar ratio of active substance to carrier protein in the conjugates is preferably 1:1000 to 2:1, in particular 1:100 to 1.1, particularly preferably 0.9 to 1.1:1. Thus, for example, albumin still shows native behavior with a 1:1 loading with methotrexate. A dose unit of active substance is preferably from 0.1 to 100 mg per kg of body weight, preferably 1 to 10 mg per kg of body weight, with low dose units of ≦5 mg, in particular ≦2 or ≦1 mg per kg of body weight often being particularly preferred. Owing to the long residence time of the conjugates in humans, moreover, administration of a maximum of one dose unit per day, preferably per week, more preferably per two weeks, is sufficient. For animals, e.g. mice, preferably one dose unit is administered per day.

Efficient covalent coupling of the active substance to the carrier molecule (that is to say the protein) is important for preparing the conjugates employed according to the invention. The coupling must not in particular be associated with an unwanted alteration in the carrier protein or/and the active substance. The activation of carboxyl group-containing organic compounds which has been customary to date with dicyclohexylcarbodiimide (DCC) takes more than 12 hours at room temperature or at +4° C. (DP 41 22 210 A1; EP 0 879 604 A1; EP 0 820 308). In this method moreover the activation is associated with the formation of insoluble substances which precipitate partly even during the activation and partly when the activated active substance is introduced into an aqueous protein solution and, in order for it to be possible to administer the conjugate medicinally, must be removed by time-consuming and costly filtration steps in addition to the actual product purification, and never are 100% (because of the lipophilic domains in albumin).

There has therefore been a need to provide a method for preparing active substance-protein conjugates with which these problems do not occur and with which in particular no water-insoluble by-products are formed.

This object has been achieved according to the invention by a method for preparing a conjugate comprising i) a carboxyl group-containing organic compound, in particular methotrexate and ii) a protein, in particular albumin, which is characterized in that a carboxyl group-containing organic compound and a protein are reacted in the presence of 1-ethyl-3-(3-dimethylaminopropyl)carbodiimide and of N-hydroxysuccinimide.

It has surprisingly been found that by using 1-ethyl-3-(3-dimethylaminopropyl)carbodiimide (EDC), especially in the form of the hydrochloride, it is possible to achieve an activation of the carboxyl group-containing organic compound and a reaction with a carrier protein without the formation of water-insoluble by-products requiring time-consuming and costly removal. Intermediate purification steps are unnecessary with this method, and the preparation time and thus also the preparation costs are substantially reduced. In addition, problems caused by insoluble substances or by-products on injection of the conjugate into a human or animal body are avoided.

The activation preferably takes place at a temperature of from 10 to 100° C., more preferably 20 to 70° C. and even more preferably 40 to 65° C., for a reaction time of from 1 minute to 10 hours, more preferably from 10 to 30 minutes. The reaction of the activated active substance with the carrier protein preferably takes place at a temperature of between 10 and 50° C., in particular between 20 and 40° C.

The activation of the carboxyl-containing compound, in particular of methotrexate, with 1-ethyl-3-(3-dimethylaminopropyl)carbodiimide and N-hydroxysuccinimide is preferably carried out in an organic solvent, preferably in dimethylacetamide. Further suitable organic solvents are, for example, DMSO (dimethyl sulfoxide) or dioxane. The activation is preferably carried out with exclusion of water, in particular in the presence of ≦5% by weight water, more preferably ≦1% by weight water and most preferably completely anhydrous. Through activation of the carboxyl group-containing compound with the substances EDC and N-hydroxysuccinimide employed in an organic, anhydrous solvent, they do not react with protein, e.g. albumin, and do not alter its structure either.

A substantial advantage of the preparation method of the invention is that the activating reagents employed, that is to say 1-ethyl-3-(3-dimethylaminopropyl)carbodiimide and N-hydroxysuccinimide, have a high solubility in water. It is thus possible for coupling reagents not consumed in the reaction to be removed in a simple manner from the product obtained, for example by washing with water. In contrast thereto, with the coupling reagents used in the prior art, for example on use of dicyclohexylcarbodiimide (DCC), an unremovable residue of coupling reagent remains in the conjugate. Thus, with a methotrexate-albumin conjugate and use of DCC, an unremovable residue of about 13 to 15% by weight of DCC is to be observed in the conjugate and is probably bound to a lipophilic domain in the albumin. This residue can be detected only with the aid of HPLC and can be removed preparatively only with considerable complexity.

A further preferred aspect of the invention relates to an optimized preparation method for a conjugate of the invention comprising i) a carboxyl group-containing organic compound and ii) a protein, which is characterized in that a carboxyl group-containing organic compound and a protein are reacted in the presence of 1-ethyl-3-(3-dimethylaminopropyl)carbodiimide.

In a preferred embodiment, the carboxyl group-containing organic compound is preferably a cytostatic or immunosuppressant, particularly preferably methotrexate, aminopterin and/or N-phthaloyl-L-glutamic acid, particularly preferably methotrexate. The protein is preferably albumin.

It has surprisingly been found that the optimized method which operates without N-hydroxysuccinimide has a beneficial effect on simplifying the preparation in the purification procedure. Through the use of 1-ethyl-3-(3-dimethylaminopropyl)carbodiimide hydrochloride (EDC) for activation without the addition of N-hydroxysuccinimide (HSI), the activation time for aminopterin (AMPT), methotrexate (MTX) and N-phthaloyl-L-glutamic acid (NPLG) is still only 10 minutes. A further advantage of the optimized method without N-hydroxysuccinimide is that a direct check of the coupling efficiency is possible after addition of the activated active substances AMPT, MTX or NPLG to the submitted protein, in particular albumin. When N-hydroxysuccinimide is used, this likewise has a high UV absorption in the HPLC when the UV measuring cell is set at 280 nm and, through its retention time of about 11.5 minutes, at which other low molecular weight compounds also appear, impairs or impedes direct determination of the coupling yield. This means that in many cases a determination of the yield is possible only at the end of the purification of the conjugate. This factor can now be eliminated through the optimized method without use of N-hydroxysuccinimide. This is also a great advantage for product safety. A further advantage of the optimized method is that the coupling yield surprisingly averages 98 to 99%.

The overall costs of the particular conjugate are thus distinctly reduced by this simplification of the preparation.

In the reaction according to the invention the carboxyl group-containing organic compound, in particular methotrexate, and the protein, in particular albumin, are employed in a molar ratio of from 10:1 to 1:10, in particular 1.5:1 to 1:1.5.

The conjugates prepared by the method of the invention can, because of their high purity, be provided for numerous uses and in particular for intravenous administration. Thus, such conjugates, for example when a carboxyl group-containing organic compound having an immunosuppressive action is used, can advantageously be employed for producing pharmaceuticals for modulating a transplantation-associated immune response, in particular for producing a pharmaceutical for the prophylaxis or/and treatment of GVHD. However, it is also possible by using carboxyl group-containing organic compounds having a cytostatic effect to produce a pharmaceutical for the treatment or/and prophylaxis or/and diagnosis of neoplastic diseases. Conjugates prepared according to the invention are also suitable for producing pharmaceuticals for the treatment or/and diagnosis of inflammatory, infectious and/or skin diseases.

The invention is illustrated further by the following examples and the appended figures.

EXAMPLE 1

Preparation Example

Methotrexate (MTX) is activated using 1-ethyl-3-(3-dimethylaminopropyl)carbodiimide hydrochloride (EDC) and N-hydroxysuccinimide (HSI) and then reacted with albumin (HSA) to give MTX-HSA.

Methotrexate Activation:

20 mg of methotrexate (MTX; FG: 454, 45; Sigma-Aldrich, Taufkirchen) are dissolved together with 25 mg of 1-ethyl-3-(3-dimethylaminopropyl)carbodiimide hydrochloride (EDC, FW: 191.7, Sigma-Aldrich, Taufkirchen) and 60 mg of N-hydroxysuccinimide (HSI, FW: 115.1; Sigma-Aldrich, Taufkirchen) in 2 ml of dimethylacetamide (DMAA). The reaction mixture is put into a water bath preheated to 60° C. After a reaction time of about 30 min, the activation solution is cooled to room temperature and then slowly introduced into a 5% HSA solution (10 ml of 20% original HSA solution are diluted with 30 ml of dist. H2O).

The additional substances necessary for the coupling of MTX (DMAA, HSI, dimethylurea and unbound methotrexate) are removed by ultrafiltration (dialysis) with a cutoff of 30 KD (YM 30).

Purity Check (HPLC):

| Precolumn: | 25 × 10 mm LiChrospher DIOL, 5 μm |
| Column: | 250 × 10 mm LiChrospher DIOL, 5 μm |

-continued

| | |
|---|---|
| Mobile phase: | Na citrate, 02 M, pH 7.4 |
| Flow rate: | 1.0 ml/min |
| Pressure: | about 95 bar |
| UV monitor: | 280 nm |

Retention Times:

| | |
|---|---|
| dimeric SA fraction | 5.8 min |
| monomeric SA fraction | 7.0 min |
| low molecular weight MTX | 33.8 min |

Figure 1:
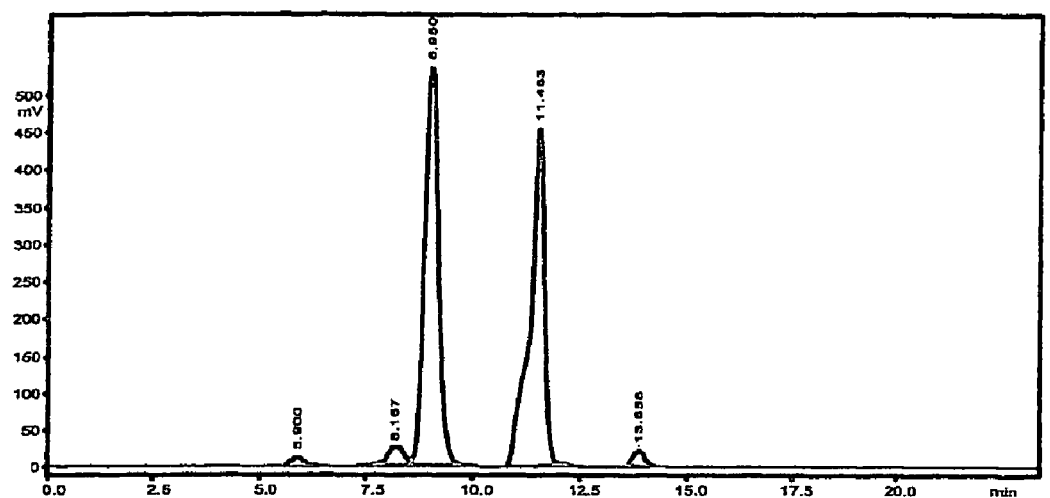
FIG. 1 shows an HPLC chromatogram of the methotrexate-human serum albumin (MTX-HSA) conjugate prepared according to example 1, which operates by the preparation method using N-hydroxysuccinimide (NHSI) and thus the synthesis of a reactive ester as intermediate.

Chromatogram: see FIG. 1

EXAMPLE 2

Animal experiments: (authorization No. LVL M-V310-4/7221.3-1.2-015/03 Landesveterinäramt Mecklenburg-Vorpommern Rostock)

Initial statistically significant experiments with the long-circulating macromolecular MTX-HSA in GVHD animals were carried out in the department of Prof. Dr. M. Freund in Rostock University clinic under the direction of PD Dr G. Hartung and Dr D. Wolff. These entailed 20 female F1 hybrid BN/Lew rats receiving whole-body irradiation with 7.5 Gy (n=10) or 9 Gy (n=10) and then transplantation of 40 million bone marrow cells and 15 million T lymphocytes from female Lew rats. 10 rats received on day 0, 4, 8 and 12 in each case 2 mg/kg methotrexate-albumin intraperitoneally, while a further 10 rats received only the equivalent amount of albumin intraperitoneally at identical times. It was possible to demonstrate in the result that only one rat from the group which received methotrexate-albumin developed an acute GVHD, while all the animals in the control group died of the consequences of an acute GVHD. No significant side effect of methotrexate-albumin were detectable, whereas distinct side effect were to be observed both animals treated with equieffective MTX doses.

EXAMPLE 3

Optimized Preparation Example

Methotrexate (MTX) is dissolved together with 1-ethyl-3-(3-dimethylaminopropyl)carbodiimide hydrochloride (EDC) in DMSO, brought to reaction (activated) by heating and then reacted with albumin (HSA) to give MTX-HSA.

Methotrexate Activation:

20 mg of methotrexate (MTX; FG: 454, 45; Sigma-Aldrich, Taufkirchen) are dissolved together with 25 mg of 1-ethyl-3-(3-dimethylaminopropyl)carbodiimide hydrochloride (EDC, FW: 191.7, Sigma-Aldrich, Taufkirchen) in 1 ml of dimethyl sulfoxide (DMSO). The reaction mixture is put into a water bath preheated to 65° C. After a reaction time of about 10 minutes, the activation solution is cooled to room temperature and then slowly introduced into a 5% HSA solution (10 ml of 20% original HSA solution are diluted with 30 ml of dist. water).

The additional substances (DMSO, ethyl-3-dimethylaminopropylurea and unbound active substance) necessary for coupling MTX (AMPT or NPLG) are removed by ultrafiltration (dialysis) with a cutoff of 30 KD (YM 30, Millipore).

Figure 2:
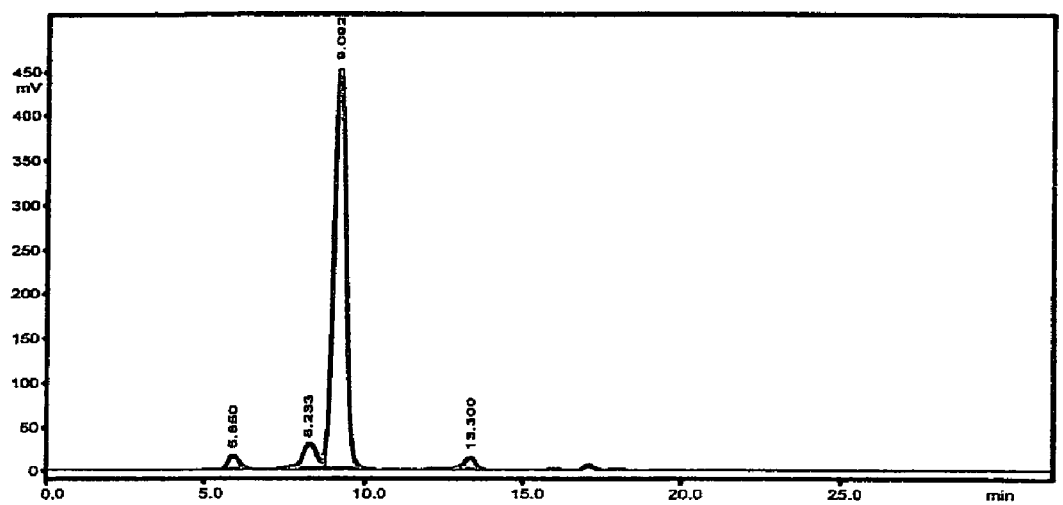
FIG. 2 shows the chromatogram of the MTX-HSA conjugate prepared according to example 3 without use of NHSI, utilizing the carboxyl group activated by 1-ethyl-3-(3-dimeethylaminopropyl)carbodiimide hydroxychloride (EDC) directly for coupling of the MTX.

Purity Check (HPLC):

| | |
|---|---|
| Precolumn: | Reprosil 200 SEC, 5 × 4 mm, 5 μm (Dr Maisch) |
| Column: | Reprosil 200 SEC, 300 × 4.6 mm, 5 μm (Dr Maisch) |
| Mobile phase: | Na$_2$HPO4, 0.19 M, pH 7.4 with 5% methanol |
| Flow rate: | 0.3 ml/min |
| Pressure: | about 51 bar |
| Retention times: | |
| dimeric SA fraction | 8.2 min |
| monomeric SA fraction | 9.1 min |
| low molecular weight MTX | 13.3 min |
| Chromatogram: | see FIG. 2 |

The invention claimed is:

1. A method for preventing a transplantation-associated immune response in a subject, comprising:
    administering to said subject an effective amount of a conjugate comprising methotrexate and albumin at a methotrexate:albumin molar ratio of 0.9 to 1.1:1,
    wherein said transplantation is an organ transplantation selected from the group consisting of kidney, heart and liver transplantation.

2. The method of claim 1, wherein said transplantation-associated immune response is graft versus host disease (GVHD).

3. The method of claim 2, wherein said GVHD is an acute GVHD.

4. The method of claim 2, wherein said GVHD is a chronic GVHD.

5. The method of claim 1, wherein said transplantation is an allogeneic transplantation.

6. The method of claim 1, wherein said albumin is human albumin.

7. The method of claim 1, wherein said albumin is a native human albumin.

* * * * *